United States Patent
Müller et al.

(10) Patent No.: US 11,992,556 B2
(45) Date of Patent: *May 28, 2024

(54) PHARMACEUTICAL AEROSOL PRODUCT FOR ADMINISTRATION BY ORAL OR NASAL INHALATION

(71) Applicant: Covis Pharma GmbH, Zug (CH)

(72) Inventors: Helgert Müller, Radolfzell (DE); Renate Engelstätter, Allensbach (DE); Ulrich Bildmann, Hilzingen (DE); Andrea Bauer, North Reading, MA (US); Paul McGlynn, Northborough, MA (US)

(73) Assignee: Covis Pharma GmbH, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/319,655

(22) Filed: May 13, 2021

(65) Prior Publication Data

US 2021/0267888 A1 Sep. 2, 2021

Related U.S. Application Data

(63) Continuation of application No. 14/238,055, filed as application No. PCT/EP2012/065812 on Aug. 13, 2012, now Pat. No. 11,007,150.

(60) Provisional application No. 61/524,803, filed on Aug. 18, 2011.

(30) Foreign Application Priority Data

Aug. 19, 2011 (EP) ........................ 1178042

(51) Int. Cl.

| A61K 9/12 | (2006.01) |
| A61K 9/00 | (2006.01) |
| A61K 31/58 | (2006.01) |
| A61M 11/04 | (2006.01) |
| A61M 15/00 | (2006.01) |

(52) U.S. Cl.
CPC ............ *A61K 9/124* (2013.01); *A61K 9/008* (2013.01); *A61K 31/58* (2013.01); *A61M 11/04* (2013.01); *A61M 15/0001* (2014.02); *A61M 15/0065* (2013.01); *A61M 15/009* (2013.01)

(58) Field of Classification Search
CPC ........ A61K 9/124; A61K 31/58; A61K 9/008; A61M 15/0001; A61M 11/04; A61M 15/0065; A61M 15/009
See application file for complete search history.

(56) References Cited

U.S. PATENT DOCUMENTS

| 5,290,539 A | 3/1994 | Marecki |
| 5,474,758 A | 12/1995 | Kwon |
| 5,482,934 A | 1/1996 | Calatayud et al. |
| 5,622,163 A | 4/1997 | Jewett |
| 5,836,299 A | 11/1998 | Kwon |
| 5,871,007 A | 2/1999 | Clark, Jr. |
| 6,120,752 A | 9/2000 | Oliver |
| 6,264,923 B1 | 7/2001 | Oliver |
| 8,371,292 B2 | 2/2013 | Bethke |
| 11,007,150 B2 * | 5/2021 | Muller .................. A61K 9/124 |
| 2004/0023935 A1 | 2/2004 | Banerjee et al. |
| 2006/0127323 A1 | 6/2006 | Dietzel et al. |
| 2006/0151524 A1 | 7/2006 | Stradella et al. |
| 2006/0163275 A1 | 7/2006 | Stradella et al. |
| 2007/0029341 A1 | 2/2007 | Stradella et al. |
| 2007/0134165 A1 | 6/2007 | Wurst |
| 2009/0318397 A1 | 12/2009 | Lulla et al. |
| 2013/0095146 A1 | 4/2013 | Nagano |
| 2013/0143849 A1 | 6/2013 | Wurst |
| 2016/0015634 A1 | 1/2016 | Brueck-Scheffler |
| 2019/0290661 A1 | 9/2019 | Wurst |

FOREIGN PATENT DOCUMENTS

| WO | 9206675 A1 | 4/1992 |
| WO | 9211190 A2 | 7/1992 |
| WO | 9508484 A1 | 3/1995 |
| WO | 9526769 A1 | 10/1995 |
| WO | 9603172 A1 | 2/1996 |
| WO | 9632150 A1 | 10/1996 |
| WO | 9639337 A1 | 12/1996 |
| WO | 9852542 A1 | 11/1998 |
| WO | 2004110460 A1 | 12/2004 |
| WO | 2005025578 A1 | 3/2005 |
| WO | 2005060441 A2 | 7/2005 |
| WO | 2007103712 A2 | 9/2007 |

OTHER PUBLICATIONS

Sirand, Christophe, et al., "Aerosol-Filing Equipment for the Preparation of Pressurized Pack Pharmaceutical Formulations", Pharmaceutical Inhalation Aerosol Technology, 1992, pp. 187-217.

Mealy, N.E., et al., "Ciclesonide", Drugs of the Future 2001, 26(11), pp. 1033-1039.

Wilkinon, Anthony, "The Manufacture of Metered Dose Inhalers", Metered Dose Inhaler Technology, CRC Press 1997, pp. 69-116.

* cited by examiner

Primary Examiner — Shirley V Gembeh

(74) Attorney, Agent, or Firm — Lowenstein Sanlder LLP

(57) ABSTRACT

This invention relates to a pharmaceutical aerosol product suitable for administration by oral or nasal inhalation and its use in the treatment of respiratory diseases, in particular in the treatment of children. The aerosol composition comprises ciclesonide, ethanol and either 1, 1, 1, 2-tetrafluoroethane, or 1, 1, 1, 2, 3, 3, 3-heptafluoropropane.

12 Claims, No Drawings

PHARMACEUTICAL AEROSOL PRODUCT FOR ADMINISTRATION BY ORAL OR NASAL INHALATION

CROSS-REFERENCE TO RELATED APPLICATION(S)

This application is a continuation of U.S. Non-Provisional patent application Ser. No. 14/238,055, filed on Feb. 10, 2014, which is a national phase of International Application No. PCT/EP2012/065812, filed on Aug. 13, 2012, which claims the benefit of U.S. Provisional Patent Application No. 61/524,803, filed on Aug. 18, 2011 and of European Patent Application No. 11178042.5, filed on Aug. 19, 2011. The contents of these applications are hereby incorporated by reference in their entirety.

TECHNICAL FIELD

This invention relates to a pharmaceutical aerosol product suitable for administration by oral or nasal inhalation and its use in the treatment of respiratory diseases, in particular in the treatment of children.

BACKGROUND

Corticosteroids are commonly used in the treatment of a variety of respiratory diseases, such as for example asthma and allergic rhinitis. For oral inhalation, corticosteroids are generally delivered either by using a nebulizer, a metered dose inhaler, or alternatively a dry powder inhaler. For nasal administration, corticosteroids are generally delivered as intranasal sprays or nasal drops, which may be formulated with aqueous or non-aqueous vehicles.

For administration to the respiratory system of a human, it is an object to provide a pharmaceutical composition, which is both physically and chemically stable and to make available to the patient in need thereof a pharmaceutical product, which delivers with each application an accurate dose of the drug and, if applicable, displaying the targeted particle size distribution.

A pharmaceutical product for use in a specific target population might require modifications and reformulations in order to be more suitable in another target population. As an example, a dose of a drug, which is considered as a safe and effective treatment of a specific disease in adults, might not be regarded as an optimal dose with respect to safety and efficacy when applied to children, in particular younger children. For administration of a drug specifically to the paediatric population, it is an object to provide pharmaceutical compositions with low concentration of the drug and/or pharmaceutical products delivering a low dose of the drug, which low dose represents a safe and effective treatment of the targeted disease in such patient population.

The objects as outlined above are addressed and solved by the present invention.

SUMMARY

U.S. Pat. No. 5,482,934 discloses pregna-1,4-diene-3,20-dione-16-17-acetal-21 esters and their use in the treatment of inflammatory conditions. The compounds disclosed in U.S. Pat. No. 5,482,934 have the general structure of following formula I,

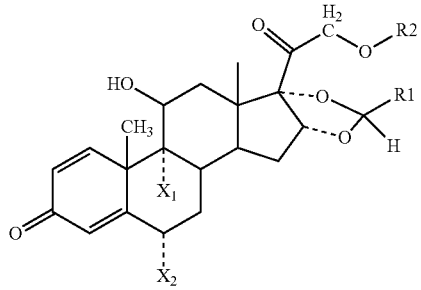

Formula I wherein R1 is a 2-propyl, 1-butyl, 2-butyl, cyclohexyl or phenyl radical; R2 is a —C(O)—CH$_3$ or —C(O)—CH(CH$_3$)$_2$ radical and in which X$_1$ and X$_2$ correspond to H or F without distinction. Ciclesonide is the INN for a compound of formula I in which R1 is cyclohexyl, R2 is a —C(O)—CH(CH$_3$)$_2$ radical and wherein both X$_1$ and X$_2$ correspond to H. Ciclesonide is characterized by the the chemical name [11β,16α(R)]-16,17-[(Cyclohexylmethylen)bis(oxy)]-11-hydroxy-21-(2-methyl-1-oxoprop-oxy)pregna-1,4-dien-3,20-dion and has the following chemical structure:

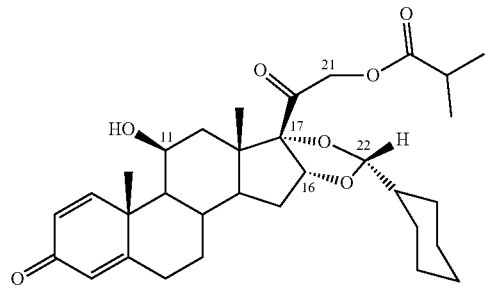 [SMILES: CC(C)C(=O)OCC(=O)[C@@]12O[C@H](C3CCCCC3)O[C@@H]1CC1C3CCC4=CC(=O)C=C[C@]4(C)C3[C@@H](O)C[C@@]12C]

U.S. Pat. No. 5,482,934 proposes a specific pressurized aerosol formulation for delivering ciclesonide for oral and nasal inhalation. The disclosed formulation consists of ciclesonide as a micronized suspension of particles, sorbitan trioleate surfactant, and a mixture of three CFC (chlorofluorocarbon) propellants: trichloro-fluoromethane, dichlorotetrafluoromethane and dichlorodifluoromethane.

U.S. Pat. No. 6,120,752 discloses a CFC-free medical aerosol product containing ciclesonide, which is suitable for delivery to the respiratory system of a patient. In particular, it discloses that ciclesonide can be formulated as a physically and chemically stable solution in formulations including hydrofluorocarbon propellants and a cosolvent, preferably ethanol, in an amount effective to solubilize ciclesonide and optionally a surfactant. The hydrofluorocarbon propellants disclosed therein include hydrofluoroalkane propellants, in particular 1,1,1,2 tetrafluorethane (Propellant 134a), 1,1,1,2,3,3,3 heptafluoropropane (Propellant 227) or a mixture thereof.

International Patent Application WO 2005/025578 discloses a method for treating or preventing a respiratory disease in children by administering ciclesonide to the children in need thereof in a dose of from 20 to 200 μg. It is further disclosed that, in a preferred embodiment, ciclesonide is administered in a composition according to U.S. Pat. No. 6,120,752.

It has now been found that ciclesonide can be formulated in low concentrations as a physically and chemically stable solution in a hydrofluorocarbon propellant. Furthermore, it has been found that respiratory diseases may be effectively and safely be treated by administering to a patient in need thereof such product with low concentration of ciclesonide, particularly when such patient is a child.

A subject matter of the present invention is a pharmaceutical composition comprising the following components:
a. ciclesonide,
b. propellant selected from 1,1,1,2-tetrafluoroethane, 1,1,1,2,3,3,3-heptafluoropropane and a mixture thereof, and
c. ethanol in an amount effective to solubilize the ciclesonide and
d. optionally a surfactant,
and wherein the concentration of ciclesonide in the composition is less than 1.0 mg per ml.

A further subject matter of the present invention is a pharmaceutical composition comprising the following components:
a. ciclesonide,
b. propellant selected from 1,1,1,2-tetrafluoroethane, 1,1,1,2,3,3,3-heptafluoropropane and a mixture thereof, and
c. ethanol in an amount effective to solubilize the ciclesonide and
d. optionally a surfactant,
and wherein the concentration of ciclesonide in the composition is from 0.1 to 0.9 mg per ml.

A further subject matter of the present invention is a pharmaceutical composition comprising the following components:
a. ciclesonide,
b. propellant selected from 1,1,1,2-tetrafluoroethane, 1,1,1,2,3,3,3-heptafluoropropane and a mixture thereof, and
c. ethanol in an amount effective to solubilize the ciclesonide and
d. optionally a surfactant,
and wherein the concentration of ciclesonide in the composition is from 0.1 to 0.8 mg per ml.

A further subject matter of the present invention is a pharmaceutical product comprising an aerosol canister equipped with a metering valve and containing a pharmaceutical composition according to the present invention.

A further subject matter of the present invention is a pharmaceutical product comprising an actuator and an aerosol canister equipped with a metering valve and containing a pharmaceutical composition according to the present invention.

A further subject matter of the present invention is a method for treating or preventing a respiratory disease in a patient, which method comprises administering to the patient a dose of a composition according to the present invention.

A further subject matter of the present invention is a pharmaceutical composition according to the present invention for use as a medicament.

A further subject matter of the present invention is a pharmaceutical composition according to the present invention for use in the treatment or prevention of respiratory diseases.

A further subject matter of the present invention is a pharmaceutical composition according to the present invention for use in the treatment or prevention of nasal symptoms associated with allergic rhinitis.

A further subject matter of the present invention is the use of a pharmaceutical composition according to the present invention in the manufacture of a medicament.

A further subject matter of the present invention is the use of a pharmaceutical composition according to the present invention in the manufacture of a medicament for the treatment or prevention of respiratory diseases.

A further subject matter of the present invention is the use of a pharmaceutical composition according to the present invention in the manufacture of a medicament for the treatment or prevention of nasal symptoms associated with allergic rhinitis.

One embodiment refers to a concentration of ciclesonide in the composition from 0.25 to 0.75 mg per ml. Another embodiment refers to a concentration of ciclesonide in the composition from 0.4 to 0.6 mg per ml. Another embodiment refers to a concentration of ciclesonide in the composition of 0.1 mg per ml. Another embodiment refers to a concentration of ciclesonide in the composition of 0.2 mg per ml. Another embodiment refers to a concentration of ciclesonide in the composition of 0.25 mg per ml. Another embodiment refers to a concentration of ciclesonide in the composition of 0.3 mg per ml. Another embodiment refers to a concentration of ciclesonide in the composition of 0.4 mg per ml. Another embodiment refers to a concentration of ciclesonide in the composition of 0.5 mg per ml. Another embodiment refers to a concentration of ciclesonide in the composition of 0.6 mg per ml. Another embodiment refers to a concentration of ciclesonide in the composition of 0.7 mg per ml. Another embodiment refers to a concentration of ciclesonide in the composition of 0.8 mg per ml. Another embodiment refers to a concentration of ciclesonide in the composition of 0.9 mg per ml.

Another embodiment refers to a pharmaceutical composition which is free or substantially free of surfactant. Another embodiment refers to a pharmaceutical composition which is free or substantially free of surfactant and free or substantially free of any other excipient.

Another embodiment refers to a pharmaceutical composition, in which the concentration of ethanol in the composition is from 10 to 300 mg per ml. Another embodiment refers to a pharmaceutical composition, in which the concentration of ethanol in the composition is from 20 to 200 mg per ml. Another embodiment refers to a pharmaceutical composition, in which the concentration of ethanol in the composition is from 25 to 130 mg per ml. Another embodiment refers to a pharmaceutical composition, in which the concentration of ethanol in the composition is from 30 to 120 mg per ml. Another embodiment refers to a pharmaceutical composition, in which the concentration of ethanol in the composition is from 40 to 150 mg per ml. Another embodiment refers to a pharmaceutical composition, in which the concentration of ethanol in the composition is from 90 to 100 mg per ml. Another embodiment refers to a pharmaceutical composition, in which the concentration of ethanol in the composition is from 91 to 93 mg per ml. Another embodiment refers to a pharmaceutical composition, in which the concentration of ethanol in the composition is from 91.5 to 92.5 mg per ml. Another embodiment refers to a pharmaceutical composition, in which the concentration of ethanol in the composition is from 30 to 90 mg per ml. Another embodiment refers to a pharmaceutical composition, in which the concentration of ethanol in the composition is from 35 to 70 mg per ml. Another embodiment refers to a pharmaceutical composition, in which the concentration of ethanol in the composition is from 40 to 60 mg per ml. Another embodiment refers to a pharmaceutical composition, in which the concentration of ethanol in the composition is from 40 to 50 mg per ml. Another embodiment refers to a pharmaceutical composition, in which the concentration of ethanol in the composition is from 50 to 60 mg per ml. Another embodiment refers to a pharmaceutical composition, in which the concentration of ethanol in the composition is from 60 to 70 mg per ml. Another embodiment refers to a pharmaceutical composition, in which the concentration of ethanol in the composition is from 70 to 80 mg per ml. Another embodiment refers to a pharmaceutical composition, in which the concentration of ethanol in the composition is from 80 to 90 mg per ml. Another embodiment refers to a pharmaceutical composition, in which the concentration of ethanol in the composition is from 90 to 100 mg per ml.

Another embodiment refers to a pharmaceutical composition, in which the propellant is 1,1,1,2-tetrafluoroethane. Another embodiment refers to a pharmaceutical composition, in which the propellant is 1,1,1,2,3,3,3-heptafluoropropane. Another embodiment refers to a pharmaceutical composition, in which the propellant is a mixture of 1,1,1,2-tetrafluoroethane and 1,1,1,2,3,3,3-heptafluoropropane. Another embodiment refers to a pharmaceutical composition, in which the propellant is a mixture of 1,1,1,2-tetrafluoroethane and 1,1,1,2,3,3,3-heptafluoropropane in a ratio between 25:75 and 75:25 w/w.

Another embodiment refers to a pharmaceutical composition, in which the propellant is 1,1,1,2-tetrafluoroethane and wherein the ratio of ethanol:1,1,1,2-tetrafluoroethane is from 2:98 by weight to 12:88 by weight. Another embodiment refers to a pharmaceutical composition, in which the propellant is 1,1,1,2-tetrafluoroethane and wherein the ratio of ethanol:1,1,1,2-tetrafluoroethane is from 3:97 by weight to 12:88 by weight. Another embodiment refers to a pharmaceutical composition, in which the propellant is 1,1,1,2-tetrafluoroethane and wherein the ratio of ethanol:1,1,1,2-tetrafluoroethane is from 3:97 by weight to 10:90 by weight. Another embodiment refers to a pharmaceutical composition, in which the propellant is 1,1,1,2-tetrafluoroethane and wherein the ratio of ethanol:1,1,1,2-tetrafluoroethane is from 3:97 by weight to 7:93 by weight. Another embodiment refers to a pharmaceutical composition, in which the propellant is 1,1,1,2-tetrafluoroethane and wherein the ratio of ethanol:1,1,1,2-tetrafluoroethane is from 3:97 by weight to 6:94 by weight. Another embodiment refers to a pharmaceutical composition, in which the propellant is 1,1,1,2-tetrafluoroethane and wherein the ratio of ethanol:1,1,1,2-tetrafluoroethane is from 3:97 by weight to 5:95 by weight. Another embodiment refers to a pharmaceutical composition, in which the propellant is 1,1,1,2-tetrafluoroethane and wherein the ratio of ethanol:1,1,1,2-tetrafluoroethane is from 3.5:96.5 by weight to 4.5:95.5 by weight. Another embodiment refers to a pharmaceutical composition, in which the propellant is 1,1,1,2-tetrafluoroethane and wherein the ratio of ethanol:1,1,1,2-tetrafluoroethane is from 7:93 by weight to 9:91 by weight. Another embodiment refers to a pharmaceutical composition, in which the propellant is 1,1,1,2-tetrafluoroethane and wherein the ratio of ethanol:1,1,1,2-tetrafluoroethane is from 7.5:92.5 by weight to 8.5:91.5 by weight. Another embodiment refers to a pharmaceutical composition, in which the propellant is 1,1,1,2-tetrafluoroethane and wherein the ratio of ethanol:1,1,1,2-tetrafluoroethane is 2:98 by weight. Another embodiment refers to a pharmaceutical composition, in which the propellant is 1,1,1,2-tetrafluoroethane and wherein the ratio of ethanol:1,1,1,2-tetrafluoroethane is 3:97 by weight. Another embodiment refers to a pharmaceutical composition, in which the propellant is 1,1,1,2-tetrafluoroethane and wherein the ratio of ethanol:1,1,1,2-tetrafluoroethane is 4:96 by weight. Another embodiment refers to a pharmaceutical composition, in which the propellant is 1,1,1,2-tetrafluoroethane and wherein the ratio of ethanol:1,1,1,2-tetrafluoroethane is 5:95 by weight. Another embodiment refers to a pharmaceutical composition, in which the propellant is 1,1,1,2-tetrafluoroethane and wherein the ratio of ethanol:1,1,1,2-tetrafluoroethane is 6:94 by weight. Another embodiment refers to a pharmaceutical composition, in which the propellant is 1,1,1,2-tetrafluoroethane and wherein the ratio of ethanol:1,1,1,2-tetrafluoroethane is 7:93 by weight. Another embodiment refers to a pharmaceutical composition, in which the propellant is 1,1,1,2-tetrafluoroethane and wherein the ratio of ethanol:1,1,1,2-tetrafluoroethane is 8:92 by weight. Another embodiment refers to a pharmaceutical composition, in which the propellant is 1,1,1,2-tetrafluoroethane and wherein the ratio of ethanol:1,1,1,2-tetrafluoroethane is 9:91 by weight. Another embodiment refers to a pharmaceutical composition, in which the propellant is 1,1,1,2-tetrafluoroethane and wherein the ratio of ethanol:1,1,1,2-tetrafluoroethane is 10:90 by weight.

Another embodiment refers to a pharmaceutical composition, comprising, essentially consisting of or consisting of
  a. ciclesonide in a concentration in the composition of 0.5 mg per ml,
  b. the propellant 1,1,1,2-tetrafluoroethane in a concentration in the composition of 1000 to 1200 mg per ml and
  c. ethanol in a concentration in the composition of 40 to 50 mg per ml.

Another embodiment refers to a pharmaceutical composition, comprising, essentially consisting of or consisting of
  a. ciclesonide in a concentration in the composition of 0.5 mg per ml,
  b. the propellant 1,1,1,2-tetrafluoroethane in a concentration in the composition of 1000 to 1200 mg per ml and
  c. ethanol in a concentration in the composition of 50 to 60 mg per ml.

Another embodiment refers to a pharmaceutical composition, comprising, essentially consisting of or consisting of
  a. ciclesonide in a concentration in the composition of 0.5 mg per ml,
  b. the propellant 1,1,1,2-tetrafluoroethane in a concentration in the composition of 1000 to 1200 mg per ml and
  c. ethanol in a concentration in the composition of 60 to 70 mg per ml.

Another embodiment refers to a pharmaceutical composition, comprising, essentially consisting of or consisting of
  a. ciclesonide in a concentration in the composition of 0.5 mg per ml,
  b. the propellant 1,1,1,2-tetrafluoroethane in a concentration in the composition of 1000 to 1200 mg per ml and
  c. ethanol in a concentration in the composition of 70 to 80 mg per ml.

Another embodiment refers to a pharmaceutical composition, comprising, essentially consisting of or consisting of
  a. ciclesonide in a concentration in the composition of 0.5 mg per ml,
  b. the propellant 1,1,1,2-tetrafluoroethane in a concentration in the composition of 1000 to 1200 mg per ml and
  c. ethanol in a concentration in the composition of 80 to 90 mg per ml.

Another embodiment refers to a pharmaceutical composition, comprising, essentially consisting of or consisting of
  a. ciclesonide in a concentration in the composition of 0.5 mg per ml, b. the propellant 1,1,1,2-tetrafluoroethane in a concentration in the composition of 1000 to 1200 mg per ml and
c. ethanol in a concentration in the composition of 90 to 100 mg per ml.

Another embodiment refers to a pharmaceutical composition, comprising, essentially consisting of or consisting of
a. ciclesonide in a concentration in the composition of 0.5 mg per ml,
b. the propellant 1,1,1,2,3,3,3-heptafluoropropane in a concentration in the composition of 1200 to 1400 mg per ml and
c. ethanol in a concentration in the composition of 40 to 50 mg per ml.

Another embodiment refers to a pharmaceutical composition, comprising, essentially consisting of or consisting of
a. ciclesonide in a concentration in the composition of 0.5 mg per ml,
b. the propellant 1,1,1,2,3,3,3-heptafluoropropane in a concentration in the composition of 1300 to 1400 mg per ml and
c. ethanol in a concentration in the composition of 50 to 60 mg per ml.

Another embodiment refers to a pharmaceutical composition, comprising, essentially consisting of or consisting of
a. ciclesonide in a concentration in the composition of 0.5 mg per ml,
b. the propellant 1,1,1,2,3,3,3-heptafluoropropane in a concentration in the composition of 1200 to 1400 mg per ml and
c. ethanol in a concentration in the composition of 60 to 70 mg per ml.

Another embodiment refers to a pharmaceutical composition, comprising, essentially consisting of or consisting of
a. ciclesonide in a concentration in the composition of 0.5 mg per ml,
b. the propellant 1,1,1,2,3,3,3-heptafluoropropane in a concentration in the composition of 1200 to 1400 mg per ml and
c. ethanol in a concentration in the composition of 70 to 80 mg per ml.

Another embodiment refers to a pharmaceutical composition, comprising, essentially consisting of or consisting of
a. ciclesonide in a concentration in the composition of 0.5 mg per ml,
b. the propellant 1,1,1,2,3,3,3-heptafluoropropane in a concentration in the composition of 1200 to 1400 mg per ml and
c. ethanol in a concentration in the composition of 80 to 90 mg per ml.

Another embodiment refers to a pharmaceutical composition, comprising, essentially consisting of or consisting of
a. ciclesonide in a concentration in the composition of 0.5 mg per ml,
b. the propellant 1,1,1,2,3,3,3-heptafluoropropane in a concentration in the composition of 1200 to 1300 mg per ml and
c. ethanol in a concentration in the composition of 90 to 100 mg per ml.

Another embodiment refers to a pharmaceutical composition, comprising, essentially consisting of or consisting of
a. ciclesonide in a concentration in the composition of 0.5 mg per ml,
b. the propellant 1,1,1,2,3,3,3-heptafluoropropane in a concentration in the composition of 1200 to 1300 mg per ml and
c. ethanol in a concentration in the composition of 100 to 110 mg per ml.

The formulations according to the present invention can be prepared by adding the required quantity of ciclesonide into an aerosol vial, crimping a metering valve on the vial and introducing under pressure a pre-mixed blend of the propellant and the ethanol through the valve at temperatures close to ambient. In order to dissolve the ciclesonide in the blend of propellant and ethanol, the vial can for example be placed in an ultrasonic bath.

Alternatively, the formulations according to the present invention can be prepared by preparing a ciclesonide concentrate with ethanol while stirring, filling this concentrate into an aerosol vial, crimping a metering valve on the vial and subsequently introducing under pressure the propellant through the valve at temperatures close to ambient.

Alternatively, the formulations according to the present invention can be prepared by preparing a ciclesonide concentrate with ethanol while stirring and mixing this concentrate with the propellant, which propellant is liquefied by cooling below the boiling of the propellant in a refrigerated batching vessel. The resulting formulation is supplied to the filling line where the required quantity of the formulation is subsequently filled into an empty aerosol vial and a metering valve is then crimped onto the filled canister.

Canisters to be used in connection with the pharmaceutical formulation according to the invention generally comprise a container capable of withstanding the vapour pressure of the propellant, such as plastic (for example polyethylene-terephtalate) or plastic-coated glass bottle or a metal canister, for example an aluminium canister which may optionally be anodised, lacquer-coated and/or plastic-coated, which container is closed with a suitable metering valve. Canisters may be coated with a fluorocarbon polymer as described in WO 96/32150, for example, a co-polymer of polyethersulphone (PES) and polytetrafluoroethylene (PTFE). Another polymer for coating that may be contemplated is FEP (fluorinated ethylene propylene).

A metering valve is used to close the canisters containing the pharmaceutical formulation according to the invention. These metering valves are designed to deliver a metered amount of the formulation each time the valve undergoes an actuation. A suitable metering dose dispensing valve comprises a valve ferrule having a rim and associated rim gasket for engaging the aerosol vial and an aperture therethrough. Further details of valves which are suitable to be used in connection with the formulation according to the invention are known and are disclosed for example in U.S. Pat. No. 6,120,752, column 3, line 13-column 4, line 57.

The metering valve comprises a gasket, which is suitable to prevent leakage of propellant through the valve. The gasket may comprise any suitable elastomeric material such as for example low density polyethylene, chlorobutyl, nitrile rubber [synthetic rubber copolymer of acrylonitrile (2-propenenitrile) and various budadiene monomers, such as 1,2-butadiene and/or 1,3-butadiene, such as for example Type DB-218 commercially available from American Gasket & Rubber Company], butyl rubber [synthetic rubber copolymer of isobutylene and isoprene], polychloroprene [neoprene]. ethylene-butene copolymers, ethylene-octene copolymers or ethylene-hexene copolymers, such as those disclosed for example in U.S. Pat. No. 5,290,539. Thermoplastic elastomer valves as described in WO 92/11190 and valves containing EPDM [ethylene propylene diene rubber] rubber as described for example in U.S. Pat. No. 5,836,299 are likewise suitable in connection with the pharmaceutical formulation according to the invention. It is also possible that materials outlined above may be blended with one or more other polymers to achieve properties representative of the individual materials, such as disclosed for example in U.S. Pat. No. 5,474,758. Suitable valves are commercially available from manufacturers well known in the aerosol industry, for example, from Valois, France (eg. DF10, DF30, DF60), Bespak pic, UK (eg. BK300, BK356, BK357) and, by 3M Company, St. Paul, Minn., USA, (for example Spraymiser).

Valve seals, especially the gasket seal and also the seals around the metering chamber (details see U.S. Pat. No. 6,120,752 column 4, line 5-11 and associated FIG. 1), can be manufactured of a material, which is inert to and resists extraction into the contents of the formulation.

Valve materials, especially the material of manufacture of the metering chamber, can be manufactured of a material, which is inert to and resists distortion by contents of the formulation. Particularly suitable materials for use in manufacture of the metering chamber include polyesters, for example polybutyleneterephthalate (PBT) and acetals.

Materials of manufacture of the metering chamber and/or the valve stem may desirably be fluorinated, partially fluorinated or impregnated with fluorine containing substances in order to resist drug deposition.

An embodiment according to the invention comprises valves, which are entirely or at least substantially composed of metal components (e.g. commercially available Spraymiser valve, by 3M Company, St. Paul, Minn., USA).

In order to administer the pharmaceutical formulation according to the invention to a patient in need thereof, the canister is inserted into an actuator (also referred to as an actuator), which is suitable to deliver the plume of the pharmaceutical formulation ejected from the metering valve to the desired target. The actuator generally comprises a nozzle block, into which the metering valve of the canister is inserted. The nozzle block comprises an exit orifice, through which the plume of droplets of the pharmaceutical formulation is directed to a patient interface, which interface is inserted into the mouth and/or the nose of the patient for administration. In one embodiment, the actuator is designed to be suitable for oral inhalation and thus comprises a patient interface, which is a mouthpiece suitable to be inserted into the mouth. In another embodiment, the actuator is designed to be suitable for nasal administration and thus comprises a patient interface, which is a nosepiece suitable to be inserted into one nostril of the nose. Generally, a suitable nosepiece has a smaller diameter than a suitable mouthpiece. For a nosepiece an upwardly sloping nosepiece might be advantageous for ease of administration to the patient's nose.

It is known, that particularly the dimensions of the exit orifice have a significant impact on the size and velocity distribution of the droplets and thus on the fraction of the ejected pharmaceutical formulation which reaches the desired target organ. Both the length as well as the diameter of the exit orifice influence the Respirable Dose as defined in the U.S. Pharmacopeia by using, e.g. the in-vitro Anderson Cascade Impactor. Adaptations of the length and diameter of the exit orifice can be performed in order to provide a plume spray with suitable size and velocity distribution of the droplets for a given pharmaceutical formulation for application to the desired target. In general, medication delivery increases with increasing length of the exit orifice and with increasing diameter of the exit orifice. However, the Respirable dose increases with decrease of the orifice diameter. For intranasal administration, when compared to oral inhalation, it might be advantageous to reduce the velocity of the spray droplets in view of the comfort of administration, however bearing in mind the efficacy of the product.

For oral inhalation of formulations according to the invention containing from 5 to 10%, for example 8%, by weight of ethanol, good respirable doses are achieved with an orifice diameter within the range of 0.20 to 0.33 mm, for example 0.28 mm, and a length of the orifice in the range of 0.30 to 0.60 mm, for example 0.50 mm. For nasal administration of formulations according to the invention containing from 2 to 10%, for example 5%, 6%, 7% or 8%, by weight of ethanol, exemplary suitable dimensions of the exit orifice are as follows: orifice diameter within the range of 0.3 to 0.7 mm, for example 0.4 mm, 0.5 mm or 0.6 mm, and a length of the orifice in the range of 2.0 mm to 3.0 mm, for example 2.4 mm, 2.5 mm, 2.6 mm, 2.7 mm or 2.8 mm. In one embodiment, the orifice diameter is 0.4 mm and the length of the orifice is 2.6 mm, 2.7 mm or 2.8 mm. In another embodiment, the orifice diameter is 0.5 mm and the length of the orifice is 2.4 mm, 2.5 mm or 2.6 mm.

Actuators, which are suitable to deliver the plume of the pharmaceutical formulation ejected from the metering valve to the desired target, are made of a material, which is suitable for the purpose. Exemplary materials of the actuators include plastic materials such as polyethylene or polypropylene.

A difficulty arising from use of metered dose medicinal actuators is that the patient often cannot precisely determine the amount of medicament in the canister at any given time. In extreme cases, a patient, possibly in an emergency situation and requiring an immediate dose of medicament, may find that the canister will not dispense a dose because its contents have already been exhausted. In order overcome these difficulties, different types of dose counters and dose indicators have been proposed. Those types of dose counters and dose indicators, which are generally suitable to be used in connection with pressurized metered dose inhalers are also suitable to be used in connection with the actuator and canister containing the formulation according to the present invention.

A number of dose counters as add-on components, which are mounted onto the closed end of the dispensing canister have been proposed for example in WO 95/26769, WO 95/08484, WO 96/03172, WO 96/39337, WO 2007/103712, U.S. Pat. Nos. 5,622,163 and 5,871,007. An assembly of an add-on dose counter and an dispensing canister has been described for example in WO 2005/060441.

Another type of dose counters or dose indicators are integrated into the actuator, into which the canister is inserted. Such dose counters or dose indicators and their operational characteristics are disclosed for example in US 2006/0151524, US 2006/0163275 or US 2007/0029341 A1

The formulations of ciclesonide according to the present invention are administered to the patient by individual sprays ejected from the canister via the metering valve. The volume of the pharmaceutical formulation according to the present invention ejected from the canister by a single spray can be adjusted by known methods, depending inter alia from the desired amount of ciclesonide to be ejected per spray and the concentration of ciclesonide in the pharmaceutical formulation. One embodiment according to the present invention refers to a single spray ejected from the canister delivering a volume of the pharmaceutical formulation from 10 μl to 200 μl. Another embodiment according to the present invention refers to a single spray ejected from the canister delivering a volume of the pharmaceutical formulation from 20 μl to 100 μl. Another embodiment according to the present invention refers to a single spray ejected from the canister delivering a volume of the pharmaceutical formulation from 25 μl to 75 μl. Exemplary individual volumes of the pharmaceutical formulation to be delivered from the canister per spray include, but are not limited to, 10 µl, 20 µl, 25 µl, 30 µl, 35 µl, 40 µl, 50 µl, 60 µl, 63 µl, 70 µl, 75 µl and 100 µl.

The amount of ciclesonide to be ejected from the canister per spray (also referred to as the ciclesonide amount ex-valve) depends on the volume of the pharmaceutical formulation to be delivered from the canister per spray and the concentration of ciclesonide in the pharmaceutical formulation. In one embodiment, the amount of ciclesonide to be ejected per spray ranges from 5 to 100 µg. In another embodiment the amount of ciclesonide to be ejected per spray ranges from 10 to 75 µg. In another embodiment the amount of ciclesonide to be ejected per spray ranges from 20 to 50 µg Exemplary individual amounts of ciclesonide to be ejected per spray include, but are not limited to, 5 µg, 10 µg, 20 µg, 25 µg, 30 µg, 35 µg, 40 µg, 50 µg, 60 µg, 70 µg and 75 µg.

In one embodiment a volume of 100 µl of a composition with a concentration of ciclesonide of 0.25 mg per ml is ejected per spray. In another embodiment a volume of 50 µl of a composition with a concentration of ciclesonide of 0.5 mg per ml is ejected per spray. In another embodiment a volume of 50 µl of a composition with a concentration of ciclesonide of 0.4 mg per ml is ejected per spray. In another embodiment a volume of 50 µl of a composition with a concentration of ciclesonide of 0.3 mg per ml is ejected per spray. In another embodiment a volume of 50 µl of a composition with a concentration of ciclesonide of 0.2 mg per ml is ejected per spray In another embodiment a volume of 40 µl of a composition with a concentration of ciclesonide of 0.5 mg per ml is ejected per spray. In another embodiment a volume of 30 µl of a composition with a concentration of ciclesonide of 0.5 mg per ml is ejected per spray.

The amount of ciclesonide per spray, which exits from the mouthpiece or nosepiece (also referred to as the ciclesonide amount ex-actuator) is generally lower than the amount of ciclesonide ejected from the canister per spray, mainly due to deposition of ciclesonide in the mouthpiece or the nosepiece. Such deposition depends inter alia on the shape, size and dimensions of the fluid pathway within the mouthpiece or nosepiece as well as from the type of material of those parts forming the fluid pathway. In one embodiment, the amount of ciclesonide per spray, which exits from the mouthpiece or nosepiece ranges from 4 to 80 µg. In another the amount of ciclesonide per spray, which exits from the mouthpiece or nosepiece ranges from 5 to 60 µg. In another embodiment the amount of ciclesonide per spray, which exits from the mouthpiece or nosepiece ranges from 10 to 50 µg Exemplary individual amounts of ciclesonide per spray, which exits from the mouthpiece or nosepiece include, but are not limited to, 8 µg, 9 µg, 10 µg, 11 µg, 12 µg, 13 µg, 14 µg, 15 µg, 16 µg, 17 µg, 18 µg, 19 µg 20 µg, 21 µg, 22 µg, 23 µg, 24 µg, 25 µg, 26 µg, 27 µg, 28 µg, 29 µg, 30 µg, 31 µg, 32 µg, 33 µg, 34 µg, 35 µg, 36 µg, 37 µg, 38 µg, 39 µg, 40 µg, 41 µg, 42 µg, 43 µg, 44 µg, 45 µg, 46 µg, 47 µg, 48 µg, 49 µg, 50 µg, 51 µg, 52 µg, 53 µg, 54 µg, 55 µg, 56 µg, 57 µg, 58 µg, 59 µg, 60 µg, 61 µg, 62 µg, 63 µg, 64 µg, 65 µg, 66 µg, 67 µg, 68 µg and 69 µg.

In one embodiment, the pharmaceutical formulation according to the present invention is used in a continuous treatment regimen. Another embodiment relates to a treatment period of more than one day. Another embodiment relates to a treatment period of more than one week, for example a two week treatment period, a one month treatment period, a six months treatment period, a one year treatment period, a two year treatment period or a life long treatment period.

In one embodiment, the pharmaceutical formulation according to the present invention is administered once daily at any time of the day, for example either in the morning or in the evening. In another embodiment, the pharmaceutical formulation according to the present invention is administered twice daily, for example in the morning and in the evening. In another embodiment, the pharmaceutical formulation according to the present invention is administered thrice daily, for example in the morning, around noon and in the evening. During each administration, one or more sprays, for example two or three sprays, can be applied. For example, one or more, for example two or three, sprays can be administered consecutively within a short period of time, for example within one hour or less, within 30 minutes or less, within 10 minutes or less or within one minute or less, in a once daily dosing regimen.

In case of oral inhalation, the pharmaceutical formulation according to the present invention can be administered according to the specific, individual circumstances and the requirements of the patient in need thereof. In one embodiment, the pharmaceutical formulation is administered by oral inhalation of one spray once daily. In another embodiment, the pharmaceutical formulation is administered by oral inhalation of more than one spray once daily, for example two or three consecutive sprays once daily.

In another embodiment the pharmaceutical formulation is administered by oral inhalation of one spray more than once daily, for example one spray twice daily (i.e. one spray in the morning and one spray in the evening) or one spray thrice daily (i.e. one spray in the morning, one spray around noon and one spray in the evening). In another embodiment the pharmaceutical formulation is administered by oral inhalation of two or more sprays twice daily, for example two or three consecutive sprays twice daily (i.e. two sprays in the morning and two sprays in the evening, or three sprays in the morning and three sprays in the evening).

In case of nasal administration, the pharmaceutical formulation according to the present invention can be administered according to the specific, individual circumstances and the requirements of the patient in need thereof. In one embodiment, the pharmaceutical formulation is administered by nasal administration to one nostril of the nose but not to the other nostril, either once daily or more once daily, for example twice or thrice daily. In another embodiment, the pharmaceutical formulation is administered by nasal administration consecutively to both nostrils of the nose either once daily or more than once daily, for example twice or thrice daily. In case of such consecutive administration to both nostrils of the nose, one or more sprays of the pharmaceutical formulation is administered to one nostril and consecutively, one or more sprays of the pharmaceutical formulation is administered to the other nostril. In a further embodiment, one spray of the pharmaceutical formulation is administered to both nostrils once daily. In a further embodiment, one spray of the pharmaceutical formulation is administered to both nostrils twice daily, for example one spray to each nostril in the morning and one spray to each nostril in the evening. In a further embodiment two sprays of the pharmaceutical formulation is administered to both nostrils once daily, for example two sprays to each nostril either in the morning or in the evening. In a further embodiment, two sprays of the pharmaceutical formulation is administered to both nostrils twice daily, for example two sprays to each nostril in the morning and two sprays to each nostril in the evening.

The total daily dose of ciclesonide administered to the patient in need thereof depends on various parameters of the dosing regimen, such as dosing frequency (once daily or more than once daily, for example twice daily or thrice daily), number of sprays per administration (for example one spray per administration, more than one spray, for example two or three consecutive sprays, per administration), volume of the pharmaceutical formulation to be delivered from the canister per spray and concentration of ciclesonide in the pharmaceutical formulation. Furthermore, mainly due to deposition of ciclesonide in the mouthpiece or the nosepiece, the total daily dose of ciclesonide administered to the patient is generally lower than the total daily dose of ciclesonide ejected from the canister. In one embodiment, the total daily dose of ciclesonide administered to the patient in form of the pharmaceutical formulation according to the present invention ranges from 5 to 400 µg. In another embodiment the total daily dose of ciclesonide ranges from 10 to 200 µg. In another embodiment the total daily dose of ciclesonide ranges from 15 to 100 µg. Exemplary individual values of total daily doses of ciclesonide include, but are not limited to 16 µg, 17 µg, 18 µg, 19 µg 20 µg, 21 µg, 22 µg, 23 µg, 24 µg, 25 µg, 26 µg, 27 µg, 28 µg, 29 µg, 30 µg, 31 µg, 32 µg, 33 µg, 34 µg, 35 µg, 36 µg, 37 µg, 38 µg, 39 µg, 40 µg, 41 µg, 42 µg, 43 µg, 44 µg, 45 µg, 46 µg, 47 µg, 48 µg, 49 µg, 50 µg, 51 µg, 52 µg, 53 µg, 54 µg, 55 µg, 56 µg, 57 µg, 58 µg, 59 µg, 60 µg, 61 µg, 62 µg, 63 µg, 64 µg, 65 µg, 66 µg, 67 µg, 68 µg, 69 µg, 70 µg, 71 µg, 72 µg, 73 µg, 74 µg, 75 µg, 76 µg, 77 µg, 78 µg, 79 µg, 80 µg, 81 µg, 82 µg, 83 µg, 84 µg, 85 µg, 86 µg, 87 µg, 88 µg, 89 µg, 90 µg, 91 µg, 92 µg, 93 µg, 94 µg, 95 µg, 96 µg, 97 µg, 98 µg and 99 µg.

In the context of the present invention, a specific numerical value (i.e. either individual values as such or a value defining the starting or end point of a range) outlined to characterize the pharmaceutical composition, the pharmaceutical product, the method of treatment or any other aspect of the present invention has to be understood to be an approximation. Therefore, in case a specific numerical value is discloses herein, such numerical value is meant and understood to be modified by the term "about". In the context of the present invention, the term "about" in connection with a specific numerical value has to be understood to include a range of +/−10 percent of the given, specific numerical value. If for example an individual value of "50" is disclosed herein, such value has to be understood as "about 50". "About 50" thereby defines any possible value in the range of +/−10 percent of 50, i.e. a range of "45 to 55". If for example a range of "from 50 to 100" is disclosed herein, such range has to be understood as "from about 50 to about 100". "About 50 to about 100" thereby defines any possible value in the range of "between 45 and 55 to 90 and 110".

Child in connection with the present invention refers to a human below eighteen years, for example seventeen years, fifteen years, twelve years, ten years, nine years, five years, two years, one year etc. One group of children according to the present invention refers to children two years of age and older, for example two years, four years, six years, ten years, eleven years, twelve years, fifteen years and seventeen years etc. Another group of children according to the present invention refers to children six years of age and older, for example six years, nine years, ten years, twelve years, fifteen years and seventeen years etc. Another group of children according to the present invention refers to children twelve years of age and older, also referred to as adolescents, i.e. children with the age of twelve years, thirteen years, fourteen years, fifteen years, sixteen years and seventeen years.

Ciclesonide has been described for use in the treatment of respiratory diseases. Therefore, formulations of ciclesonide according to the present invention have use in the treatment and prevention of clinical conditions for which a glucocorticosteroid is indicated. The formulations of ciclesonide according to the present invention are useful in the treatment and prevention of diseases associated with reversible airways obstruction such as asthma (including mild, moderate and severe persistent asthma), nocturnal asthma, exercise-induced asthma, chronic obstructive pulmonary diseases (COPD) (e.g. chronic and wheezy bronchitis, emphysema), respiratory tract infection and upper respiratory tract disease, for example allergic rhinitis (including seasonal allergic rhinitis (SAR) and perennial allergic rhinitis (PAR)). As illustrative examples, the formulations of ciclesonide according to the present invention are useful in the treatment of symptoms associated with seasonal allergic rhinitis (SAR) and perennial allergic rhinitis (PAR) or in the maintenance treatment of asthma or in the treatment to control persistent asthma.

EXAMPLES

Ciclesonide can be provided as a pharmaceutical product comprising an aerosol vial equipped with a dispensing valve. Further, ciclesonide can be provided as a pharmaceutical product comprising an actuator and an aerosol vial equipped with a dispensing metering valve. The following compositions further illustrate the present invention in terms of exemplary formulations and ingredients. However, it will be understood that the invention is not limited to these specific embodiments.

| Composition 1 | | |
| --- | --- | --- |
| Ingredient | mg per ml | % w/w |
| Ciclesonide | 0.50 | 0.04 |
| Ethanol | 94.84 | 8.00 |
| 1,1,1,2-Tetrafluoroethane (Propellant 134a) | 1090.66 | 91.96 |
| Total | 1186.00 | 100 |

| Composition 2 | | |
| --- | --- | --- |
| Ingredient | mg per ml | % w/w |
| Ciclesonide | 0.25 | 0.02 |
| Ethanol | 94.88 | 8.00 |
| 1,1,1,2-Tetrafluoroethane (Propellant 134a) | 1090.87 | 91.98 |
| Total | 1186.00 | 100 |

| Composition 3 | | |
| --- | --- | --- |
| Ingredient | mg per ml | % w/w |
| Ciclesonide | 0.75 | 0.06 |
| Ethanol | 94.80 | 8.00 |

| Composition 3 | | |
|---|---|---|
| Ingredient | mg per ml | % w/w |
| 1,1,1,2-Tetrafluoroethane (Propellant 134a) | 1090.45 | 91.94 |
| Total | 1186.00 | 100 |

| Composition 4 | | |
|---|---|---|
| Ingredient | mg per ml | % w/w |
| Ciclesonide | 0.50 | 0.04 |
| Ethanol | 47.42 | 3.93 |
| 1,1,1,2-Tetrafluoroethane (Propellant 134a) | 1159.08 | 96.03 |
| Total | 1207.00 | 100 |

| Composition 5 | | |
|---|---|---|
| Ingredient | mg per ml | % w/w |
| Ciclesonide | 0.50 | 0.04 |
| Ethanol | 71.13 | 5.93 |
| 1,1,1,2-Tetrafluoroethane (Propellant 134a) | 1127.37 | 94.03 |
| Total | 1199.00 | 100 |

| Composition 6 | | |
|---|---|---|
| Ingredient | mg per ml | % w/w |
| Ciclesonide | 0.50 | 0.04 |
| Ethanol | 118.55 | 10.03 |
| 1,1,1,2-Tetrafluoroethane (Propellant 134a) | 1062.95 | 89.93 |
| Total | 1182.00 | 100 |

| Composition 7 | | |
|---|---|---|
| Ingredient | mg per ml | % w/w |
| Ciclesonide | 0.50 | 0.04 |
| Ethanol | 55.32 | 4.00 |
| 1,1,1,2,3,3,3 heptafluoropropane (Propellant 227) | 1327.18 | 95.96 |
| Total | 1383.00 | 100 |

| Composition 8 | | |
|---|---|---|
| Ingredient | mg per ml | % w/w |
| Ciclesonide | 0.50 | 0.04 |
| Ethanol | 106.08 | 8.00 |
| 1,1,1,2,3,3,3 heptafluoropropane (Propellant 227) | 1219.42 | 91.96 |
| Total | 1326.00 | 100 |

| Composition 9 | | |
|---|---|---|
| Ingredient | mg per ml | % w/w |
| Ciclesonide | 0.50 | 0.04 |
| Ethanol | 130.90 | 10.00 |
| 1,1,1,2,3,3,3 heptafluoropropane (Propellant 227) | 1177.60 | 89.96 |
| Total | 1309.00 | 100 |

| Composition 10 | | |
|---|---|---|
| Ingredient | mg per ml | % w/w |
| Ciclesonide | 0.50 | 0.04 |
| Ethanol | 101.92 | 8.00 |
| 1,1,1,2-Tetrafluoroethane (Propellant 134a) | 585.79 | 45.98 |
| 1,1,1,2,3,3,3 heptafluoropropane (Propellant 227) | 585.79 | 45.98 |
| Total | 1274.00 | 100 |

The invention claimed is:

1. A method for preparing a pharmaceutical composition, the method comprising:
   combining:
   (a) ciclesonide,
   (b) a propellant selected from 1,1,1,2-tetrafluoroethane, 1,1,1,2,3,3,3-heptafluoropropane and a mixture thereof, and
   (c) ethanol in an amount effective to solubilize the ciclesonide and
   (d) optionally a surfactant,
   wherein the concentration of ciclesonide in the composition is from 0.1 to 0.8 mg per ml, wherein the pharmaceutical composition is contained in an aerosol canister equipped with a metering valve.

2. The method of claim 1, wherein the ciclesonide is solubilized by the ethanol.

3. The method of claim 1, wherein the concentration of ciclesonide in the composition is from 0.4 to 0.5 mg per ml.

4. The method of claim 1, wherein the concentration of ethanol in the composition is from 30 to 300 mg per ml.

5. The method of claim 1, wherein the propellant is 1,1,1,2-tetrafluoroethane.

6. The method of claim 1, wherein the propellant is 1,1,1,2,3,3,3-heptafluoropropane.

7. The method of claim 1, wherein the concentration of propellant in the composition is from 1000 to 1400 mg per ml.

8. The method of claim 1, wherein the combining comprises mixing the ciclesonide and ethanol to form a concentrate, and then adding and mixing the propellant to the concentrate.

9. The method of claim 1, wherein the combining comprises mixing the ciclesonide and ethanol to form a concentrate.

10. The method of claim 9, further comprising adding the concentrate into the aerosol canister.

11. The method of claim 10, further comprising adding the propellant to the aerosol vial while under pressure.

12. The method of claim 1, wherein the ciclesonide is the sole drug in the pharmaceutical composition.

* * * * *